United States Patent [19]

Eshriqui

[11] 4,092,740
[45] June 6, 1978

[54] ARTICULATED JOINT PROSTHESIS

[76] Inventor: Salomao Eshriqui, Rua Pompeu Loureiro No. 32, Bloco B - Apt. 402, Rio de Janeiro, Brazil

[21] Appl. No.: 729,100

[22] Filed: Oct. 4, 1976

[30] Foreign Application Priority Data

Oct. 3, 1975 Brazil ............................... 750646

[51] Int. Cl.² .............................................. A61F 1/24
[52] U.S. Cl. ........................................ 3/1.911; 3/1.91; 128/92 C
[58] Field of Search .............................. 3/1.9–1.913, 3/22; 128/92 C

[56] References Cited

U.S. PATENT DOCUMENTS

| | | | |
|---|---|---|---|
| 3,772,709 | 11/1973 | Swanson | 3/1.91 |
| 3,848,276 | 11/1974 | Martinez | 3/1.911 |
| 3,909,854 | 10/1975 | Martinez | 3/1.911 |
| 3,990,117 | 11/1976 | Pritchard et al. | 3/1.91 |

*Primary Examiner*—Ronald L. Frinks
*Attorney, Agent, or Firm*—Oblon, Fisher, Spivak, McClelland & Maier

[57] ABSTRACT

An articulated joint prosthesis, and particularly a knee joint, in which the articulation between two bone penetrating elements is provided with elastic means permitting relative movements between the two said elements in senses other than that of the normal articulation, for instance, slight separations or inclinations in the plane of the pivot axis. A small play may also be incorporated in the articulation so as to permit relative torsion between the two bone penetrating elements.

9 Claims, 6 Drawing Figures

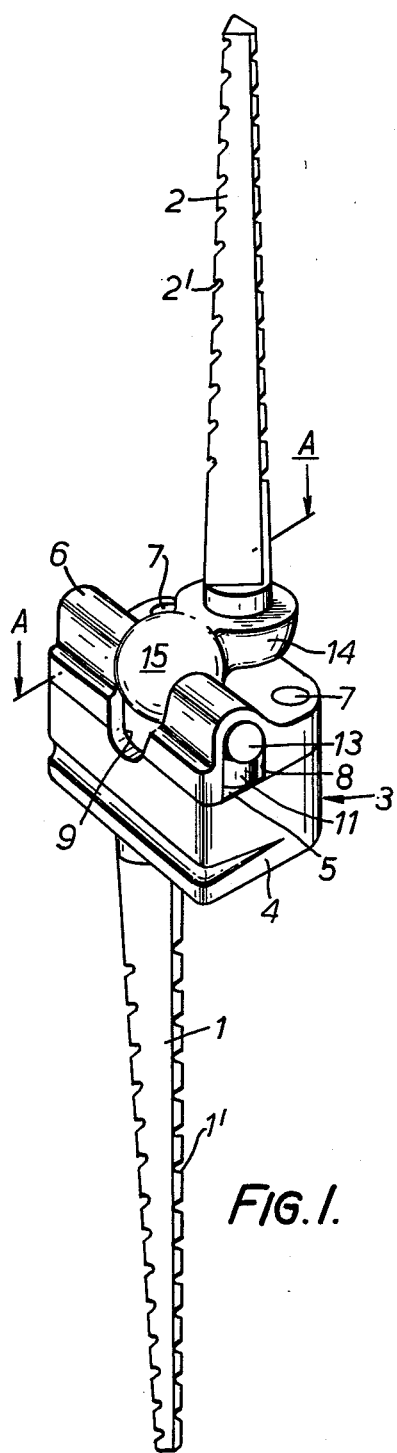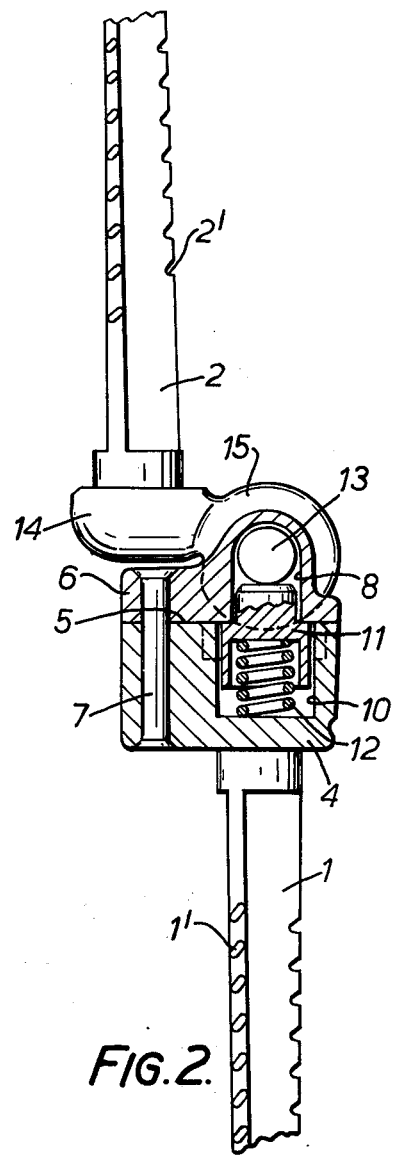

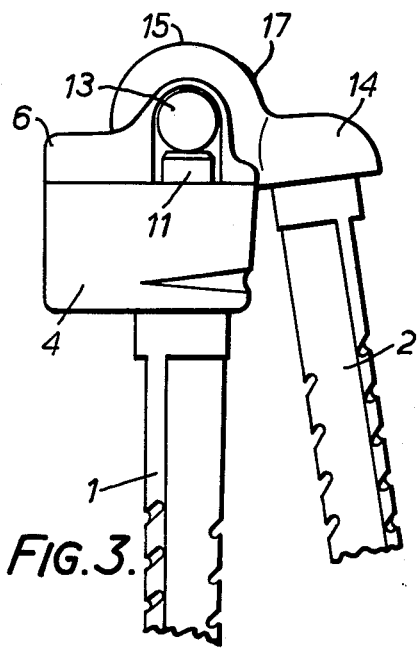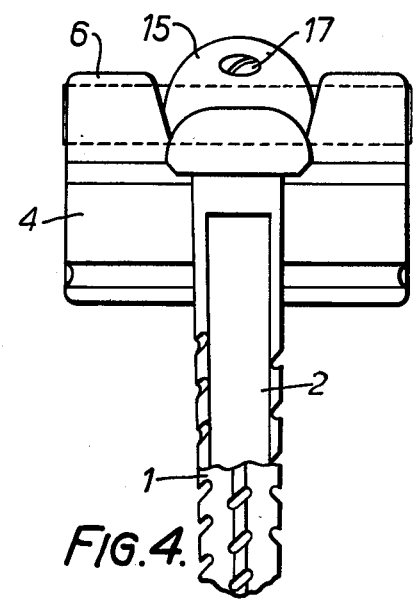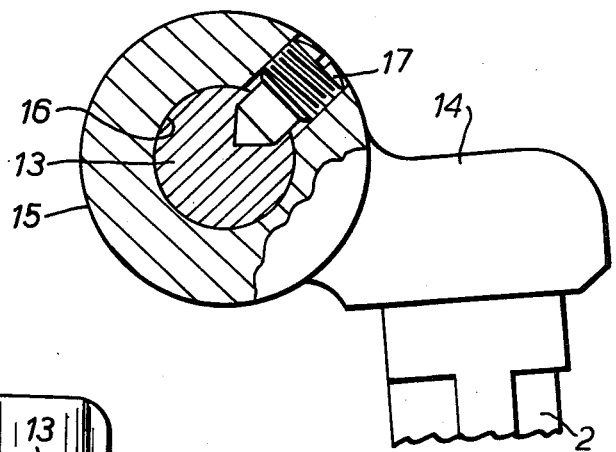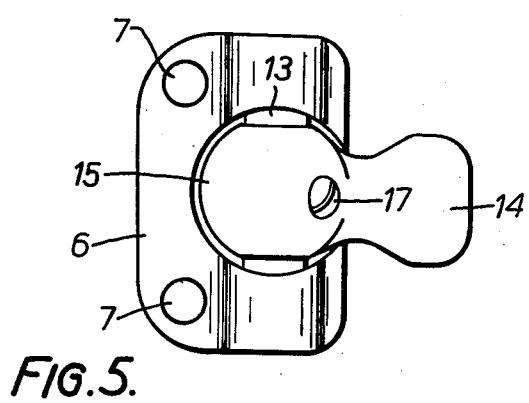

4,092,740

ARTICULATED JOINT PROSTHESIS

The present invention refers to an articulated joint prosthesis and in particular to an artificial knee.

As is well known there are many occasions in which certain joints are irreparably damaged due to damaged ligaments, particularly the knee joint of a human being, making it necessary to implant an articulated joint prosthesis with a view to restoring to the patient as perfect an articulation as possible.

The prior art articulated joint prostheses permit perfect bending movements but do not allow for any torsion, separation or lateral inclinations between the bones being joined. This leads to the disadvantage that the most frequency post-operational complication is the fracture of the femoral diaphysis which tends to occur even with minimum twisting of the patient's knee or due to excessive penetration of parts of the prosthesis in the bone during use.

It is therefore an object of the present invention to provide a relatively simple articulated joint prosthesis in which slight relative movement other than the normal articulation is permitted between the two bones being joined.

A further object of the present invention is to provide such a joint which permits slight separations between the two bones being joined at the region of the joint.

A further object of the present invention is to provide such a joint which permits slight lateral inclinations between the two bones in a plane parallel to the hinge axis of the joint.

Yet another object of the present invention is to provide an articulated joint prosthesis of the above type in which a slight relative torsion is permitted between the two bones being joined.

In accordance with the present invention an articulated joint prosthesis comprises a first bone penetrating element for penetrating the marrow of a first bone associated with one side of said joint; a second bone penetrating element for penetrating the marrow of a second bone associated with the other side of said joint; articulation means comprising first hinge means on said first element and second hinge means on said second element, said first and second hinge means being operatively associated for articulation about a hinge axis; and elastic bias means in operative relation with said first and second hinge means, permitting therebetween a limited relative movement non-parallel with respect to said hinge axis.

The invention will now be described in more detail, by way of example, with reference to the accompanying drawings in which:

FIG. 1 is a perspective view of an articulated knee joint prosthesis according to the invention in an extended position;

FIG. 2 is a cross-sectional view taken along line A—A of FIG. 1;

FIG. 3 is a side view of the joint in a bent position;

FIG. 4 is a front view of the joint in a bent position;

FIG. 5 is a plan view of the joint in a bent position, and;

FIG. 6 is a detail showing the fixation of one part of the joint to a hinge pin.

Referring now to the drawings, an articulated knee joint prosthesis made in accordance with the present invention comprises a femur penetrating element 1, a tibia penetrating element 2, and an articulation between the two, generally indicated by the reference numeral 3. Both the femur and tibia penetrating elements 1 and 2 are adapted to be forced into the marrow of the respective bone. They are relatively long tapered elements having a generally triangular cross-section, and in the embodiment shown, are formed with a series of grooves 1' and 2' in the ridges formed by the triangular section. The exact form of elements 1 and 2 may vary and the existence of grooves 1' and 2' is by no means essential.

The articulation 3 includes an upper (lower in the drawings) body part 4 in the form of a block having a planar upper surface 5. It also includes a lower (upper in the drawings) cover part 6 which is fixed to said body part 4 by means of rivets 7. The cover 6 is formed with two aligned cavities 8 which are separated by a cut-out region generally indicated by the reference numeral 9. Under each cavity 8 there is a blind bore 10 opening into planar surface 5 of body 4. Each blind bore 10 contains a spring loaded plunger 11 biased into the interior of the corresponding cavity 8 by means of a small compression spring 12. The upper or free surface of each plunger 11 forms with the interior surface of the corresponding cavity 8 a bearing for a hinge pin 13 which may comprise a steel pin within a plastic low friction sleeve of, for example, PTFE.

The lower end or the joint end of tibia penetrating element 2 is fixed to a small crank arm 14 whose free end 15 is generally spherical and provided with a diametric bore 16. Spherical part 15 is placed generally in the cut-out region 9 of cover 6 with its bore 16 aligned with cavities 8. Hinge pin 13 is passed through bore 16 and fixed to spherical end 15 by means of a fixing screw 17 as can be seen from FIGS. 3 to 6.

It will also be observed that even with the joint in an unstressed condition with plungers 11 fully extended into cavities 8, hinge pin 13 is received within the cavities with a certain tolerance or play. This tolerance or play, particularly in the lateral direction, permits a small amount of torsion between the two bone penetrating members 1 and 2. It should also be observed that the small crank arm 14 amplifies any lateral movement of the pin ends within cavities 8 and that this permits protection against accidental twisting of the joint due to a fall or the like.

The existence of the spring biased plunger arrangement 11, 12 permits greater freedom of movement of hinge pin 13 axially of the femur penetrating element 1, permitting therefore small compressions of the joint without damaging it. Equally, the fact that opposite ends of hinge pin 13 are independently mounted on separate spring loaded plungers permits small axial inclinations of the pin and therefore relative lateral rotations or oscillations (up to about 15°) of the two bone penetrating elements 1 and 2.

It should be observed also that the cut-out region 9 of cover part 6 is sufficient to permit normal movements of spherical end 15 but not large enough to allow passage therethrough of end 15 in a horizontal direction should the hinge pin break. This is a safeguard for the front of a patient's knee in such an emergency.

Although the present invention has been described with specific reference to an embodiment in the form of an artificial knee, it will be appreciated that similar principles may be used for other joints, such as the elbow or fingers either in human beings or in animals.

Obviously many modifications and variations to the artifical joint described herein will occur to those skilled in the art in the light of the above teachings. For example, although spring biased plunger arrangements have been employed, other equivalent elastic means may be provided so as to give the necessary relative movement between the two bone penetrating elements, such as compressible silicone. It is therefore to be understood that this invention may be practiced otherwise than as herein specifically described provided it be in accordance with the following claims.

I claim:

1. An articulated joint prosthesis comprising in combination:

a first bone penetrating element for penetrating the marrow of a first bone associated with one side of said joint;

a second bone penetrating element for penetrating the marrow of a second bone associated with the other side of said joint;

articulation means having a normal plane of articulation comprising first hinge means on said first element and second hinge means on said second element, said first and second hinge means being operatively associated for articulation about a hinge axis; and elastic bias means in operative relation with said first and second hinge means, permitting therebetween a limited rotational movement in a plane perpendicular to the normal plane of articulation of the articulation means;

said articulation means including a hinge pin defining said hinge axis and said bias means being positioned between said pin and said first hinge means;

said first hinge means including a bearing at each end of said pin and said bias means comprising separate elastic means forming part of each of said bearings.

2. An articulated joint prosthesis according to claim 1 in which said first hinge means comprises a part integral with said first bone penetrating element, said part defining a pair of axially aligned spaced bearing cavities and said second hinge means comprises a crank arm on said second bone penetrating element and having a free end formed with a transverse bore, said bore being placed in axial alignment with and between said cavities and transversed by said hinge pin.

3. An articulated joint prosthesis comprising in combination:

a first bone penetrating element for penetrating the marrow of a first bone associated with one side of said joint;

a second bone penetrating element for penetrating the marrow of a second bone associated with the other side of said joint;

articulation means having a normal plane of articulation comprising first hinge means on said first element and second hinge means on said second element, said first and second hinge means being operatively associated for articulation about a hinge axis; and elastic bias means in operative relation with said first and second hinge means, permitting therebetween a limited rotational movement in a plane perpendicular to the normal plane of articulation of the articulation means;

said articulation means including a hinge pin defining said hinge axis and said bias means being positioned between said pin and said first hinge means;

said first hinge means comprising a part integral with said first bone penetrating element, said part defining a pair of axially aligned spaced bearing cavities and said second hinge means comprising a crank arm on said second bone penetrating element and having a free end formed with a transverse bore, said bore being placed in axial alignment with and between said cavities and transversed by said hinge pin;

said hinge pin being removably fixed in said bore and the ends of the said hinge pin being received with a tolerance in said cavities.

4. An articulated joint prosthesis comprising in combination:

a first bone penetrating element for penetrating the marrow of a first bone associated with one side of said joint;

a second bone penetrating element for penetrating the marrow of a second bone associated with the other side of said joint;

articulation means having a normal plane of articulation comprising first hinge means on said first element and second hinge means on said second element, said first and second hinge means being operatively associated for articulation about a hinge axis; and elastic bias means in operative relation with said first and second hinge means, permitting therebetween a limited rotational movement in a plane perpendicular to the normal plane of articulation of the articulation means;

said articulation means including a hinge pin defining said hinge axis and said bias means being positioned between said pin and said first hinge means;

said first hinge means comprising a part integral with said first bone penetrating element, said part defining a pair of axially aligned spaced bearing cavities and said second hinge means comprising a crank arm on said second bone penetrating element and having a free end formed with a transverse bore, said bore being placed in axial alignment with and between said cavities and transversed by said hinge pin;

each said elastic means comprising a spring loaded element forming part of the bearing surface of the corresponding said cavity.

5. An articulated joint prosthesis according to claim 4 in which said hinge pin is fixed in said bore and the ends of the said hinge pin are received with a tolerance in said cavities so as to permit an oscillation of approximately 15° of said hinge pin in an axial plane thereof.

6. An articulated joint prosthesis comprising in combination;

a first bone penetrating element for penetrating the marrow of a first bone associated with one side of said joint;

a second bone penetrating element for penetrating the marrow of a second bone associated with the other side of said joint;

articulation means having a normal plane of articulation comprising first hinge means on said first element and second hinge means on said second element, said first and second hinge means being operatively associated for articulation about a hinge axis; and elastic bias means in operative relation with said first and second hinge means, permitting therebetween a limited rotational movement in a plane perpendicular to the normal plane of articulation of the articulation means;

said articulation means including a hinge pin defining said hinge axis and said bias means being positioned between said pin and said first hinge means;

said first hinge means comprising a part integral with said first bone penetrating element, said part defining a pair of axially aligned spaced bearing cavities and said second hinge means comprising a crank arm on said second bone penetrating element and having a free end formed with a transverse bore, said bore being placed in axial alignment with and between said cavities and transversed by said hinge pin;

said free end of said crank arm being generally spherical.

7. An articulated joint prosthesis comprising in combination:

a first bone penetrating element for penetrating the marrow of a first bone associated with one side of said joint;

a second bone penetrating element for penetrating the marrow of a second bone associated with the other side of said joint;

articulation means having a normal plane of articulation comprising first hinge means on said first element and second hinge means on said second element, said first and second hinge means being operatively associated for articulation about a hinge axis; and elastic bias means in operative relation with said first and second hinge means, permitting therebetween a limited rotational movement in a plane perpendicular to the normal plane of articulation of the articulation means;

said articulation means including a hinge pin defining said hinge axis and said bias means being positioned between said pin and said first hinge means;

said first hinge means comprising a part integral with said first bone penetrating element, said part defining a pair of axially aligned spaced bearing cavities and said second hinge means comprising a crank arm on said second bone penetrating element and having a free end formed with a transverse bore, said bore being placed in axial alignment with and between said cavities and transversed by said hinge pin;

said first hinge means member comprising a body part integral with said first bone penetrating element and a body cover part fixed to said body part, said cover part being formed with said spaced apart bearing cavities, said cavities opening towards said body part and said body part being formed with a pair of blind bores in communication, respectively, with said bearing cavities, each said blind bore containing a plunger means spring biased into the interior of said respective cavity in contact with said hinge pin.

8. An articulated joint prosthesis according to claim 7 comprising an artificial knee joint.

9. An articulated joint prosthesis according to claim 8 in which said first element is a femur penetrating element and said second element is a tibia penetrating element.

* * * * *

UNITED STATES PATENT AND TRADEMARK OFFICE
CERTIFICATE OF CORRECTION

PATENT NO. : 4,092,740
DATED : June 6, 1978
INVENTOR(S) : Salamao Eshriqui

It is certified that error appears in the above-identified patent and that said Letters Patent are hereby corrected as shown below:

Please correct the Priority Data to read as follows:

[30]   Oct. 3, 1975   Brazil....................7506468

Signed and Sealed this

*Fifteenth* Day of *May 1979*

[SEAL]

Attest:

RUTH C. MASON
*Attesting Officer*

DONALD W. BANNER
*Commissioner of Patents and Trademarks*